United States Patent
Schwander et al.

[11] 4,056,528
[45] Nov. 1, 1977

[54] DISPERSE DYES

[75] Inventors: Hansrudolf Schwander, Riehen; Kurt Burdeska, Basel; Christian Zickendraht, Binningen, all of Switzerland

[73] Assignee: Ciba-Geigy Corporation, Ardsley, N.Y.

[21] Appl. No.: 657,771

[22] Filed: Feb. 13, 1976

[30] Foreign Application Priority Data
Feb. 21, 1975 Switzerland .................. 2239/75

[51] Int. Cl.$^2$ ............................................. C07D 491/04
[52] U.S. Cl. ................................. 260/250 Q; 8/1 D
[58] Field of Search ...................... 260/250 Q, 250 QN

[56] References Cited
U.S. PATENT DOCUMENTS

| | | | |
|---|---|---|---|
| 1,762,021 | 6/1930 | Kranzlein | 260/250 Q |
| 3,399,191 | 8/1968 | Brach | 260/250 Q |

OTHER PUBLICATIONS
Klicnar et al., Chem. Abs 74, 76393d, (1971).

*Primary Examiner*—Donald G. Daus
*Assistant Examiner*—Mark L. Berch
*Attorney, Agent, or Firm*—Edward McC. Roberts; Prabodh I. Almaula

[57] ABSTRACT

A dyestuff of the formula

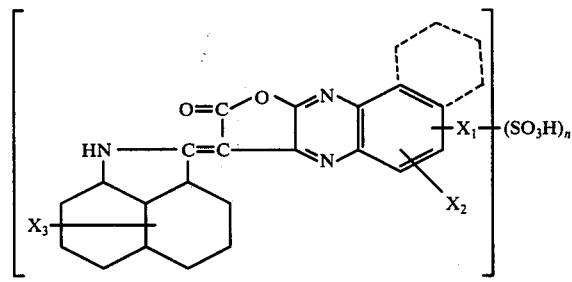

wherein $X_1$ represents fluorine, bromine, chlorine or hydrogen, $C_1$-$C_4$-alkyl, $C_1$-$C_4$-alkoxy, phenyl, phenoxy, thiophenoxy or $C_1$-$C_4$-alkyl sulphonyl, $C_1$-$C_4$-alkylthio, each of which is unsubstituted or substituted by $C_1$-$C_4$-alkoxy, hydroxy, cyano, bromine, chlorine, carbo-$C_1$-$C_4$-alkoxy, $C_1$-$C_4$-alkoxy-$C_1$-$C_4$-alkoxy, $C_1$-$C_4$-alkylcarbonyloxy, chloro-$C_1$-$C_4$-alkylcarbonyloxy or $C_1$-$C_4$-alkoxy-carbonyloxy, fluorine, bromine, chlorine, COOR, in which R represents $C_1$-$C_4$-alkyl or $C_1$-$C_4$-alkyl substituted by $C_1$-$C_4$-alkoxy, hydroxy, cyano, $C_1$-$C_4$-alkylcarbonyloxy, chlorine or bromine, —$SO_2NH$—$C_1$-$C_4$-alkyl and

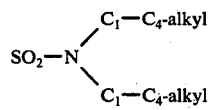

(wherein the $C_1$-$C_4$-alkyl is unsubstituted or substituted by hydroxy, chlorine, bromine, $C_1$-$C_4$-alkoxy or phenyl),
—$SO_2$-alkyl or CN;
$X_2$ represents methoxy, ethoxy, methyl or hydrogen,
$X_3$ represents hydrogen, alkyl containing up to 4 carbon atoms, chlorine, bromine,

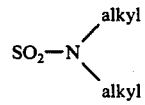

(wherein alkyl is substituted or unsubstituted), nitro, or $SO_2$—R, wherein R represents alkyl or substituted or unsubstituted phenyl, n is 0, 1 or 2, and the dotted ring can represent a fused benzene ring. The new dyestuffs dye polyester fibers in bright red shades.

8 Claims, No Drawings

DISPERSE DYES

The present invention provides dyes of formula (I)

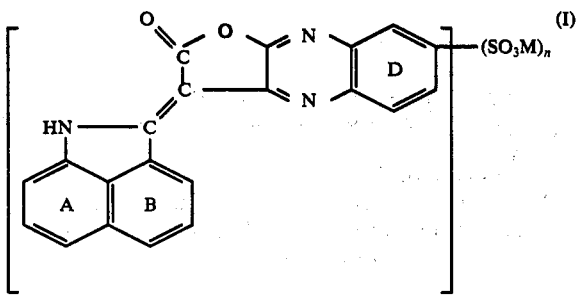

wherein $n$ is 0, 1 or 2 and the cyclic and acyclic radicals can carry non-ionogenic substituents and the ring D can additionally be fused to a benzene ring.

The dyes of the present invention are obtained by reacting a naphtholactam of formula II

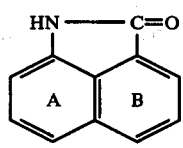

with a substituted acetic ester which contains active methylene groups of formula III

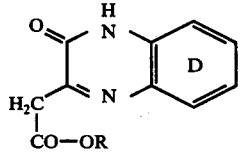

in the presence of an acid condensation agent, for example phosphoroxy chloride, at elevated temperature, and, optionally, subsequently sulphonating the reaction product.

Examples of non-ionogenic substituents at the rings A and B are: alkyl, alkoxy, halogen, nitro, alkylmercapto, alkylsulphonyl, arylsulphonyl, acylamino, cyano, carboxy amide and sulphonamide. By alkyl groups are meant those containing 1 to 4 carbon atoms, for example methyl, ethyl, isopropyl and n-butyl; and by alkoxy groups are meant those containing 1 to 4 carbon atoms, for example methoxy, ethoxy, n-propoxy, n-butoxy and isopropoxy. Halogen atoms are, besides fluorine, in particular chlorine and bromine. Alkylmercapto and alkylsulphonyl groups are in particular those containing 1 to 4 carbon atoms in the alkyl moiety, for example methylmercapto or methylsulphonyl, β-hydroxyethylmercapto or β-hydroxyethylsulphonyl, iosopropylmercapto or isopropylsulphonyl or n-butylmercapto or n-butylsulphonyl groups. By arylsulphonyl groups are meant in particular phenylsulphonyl groups and by aralkylsulphonyl preferably benzylsulphonyl groups. By acylamino is meant in particular alkylcarbonylamino groups containing 1 to 4 carbon atoms in the alkyl moiety, such as acetylamino and alkylsulphonyl-amino of 1 to 4 carbon atoms, for example methylsulphonylamino. By carboxy amide and sulphonamide groups are meant in particular those which are substituted by alkyl radicals of 1 to 4 carbon atoms, for example methyl, ethyl, n-butyl.

As examples of non-ionogenic substituents at the ring D there may be cited: alkyl, alkoxy, alkylmercapto, halogen, cyano, carboalkoxy, cycloalkyl, aralkyl, aryloxy, arylmercapto, phenyl, alkylsulphonyl, phenylsulphonyl, sulphonamide. Alkyl is to be understood in this connection as meaning in particular alkyl groups of 1 to 4 carbon atoms, such as methyl, ethyl, β-cyanoethyl, n-propyl, isopropyl and n-butyl groups as well as trifluoromethyl groups. By alkoxy, halogen, alkylsulphonyl and sulphonamide are meant in particular those groups and atoms which have been cited as suitable for rings A and B. Cycloalkyl is in particular the cyclohexyl radical and aralkyl is to be understood as meaning in particular phenylalkylene radicals of 1 to 3 carbon atoms.

Particularly useful dyes are those that contain no water-solubilising groups and have the formula

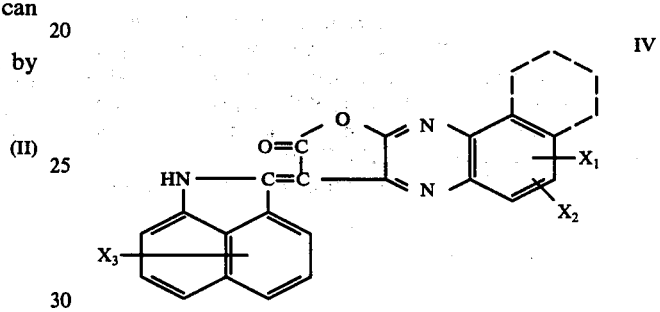

wherein $X_1$ represents hydrogen, substituted or unsubstituted alkyl, substituted or unsubstituted alkoxy, substituted or unsubstituted phenoxy, substituted or unsubstituted thiophenoxy, substituted or unsubstituted S-alkyl, halogen, preferably bromine or chlorine, COOR, in which R represents substituted or unsubstituted alkyl,

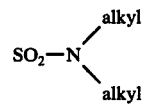

(alkyl being in each case substituted or unsubstituted), —SO$_2$-alkyl or CN, $X_2$ represents methoxy, ethoxy, methyl or preferably hydrogen, $X_3$ represents hydrogen, alkyl containing preferably up to 4 carbon atoms, chlorine, bromine,

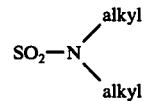

(alkyl being in each case substituted or unsubstituted), nitro, SO$_2$—R, in which R represents alkyl, substituted or unsubstituted phenyl, and alkoxy, and the dotted ring can represent a fused benzene ring.

The substituted or unsubstituted alkoxy and alkyl groups cited hereinabove contain preferably not more than 5 carbon atoms. They are also referred to hereinafter as lower alkyl and lower alkoxy groups.

The alkyl groups which can be present in the radicals $X_1$, $X_2$ and $X_3$ can be unsubstituted or substituted by alkoxy of 1 to 4 carbon atoms, chlorine, bromine, cyano, carboxyl, carbalkoxy of 1 to 4 carbon atoms, sulpho, carboxy amide or acetoxy, for example, methyl, ethyl, β-cyanoethyl, β-chloroethyl, β-hydroxyethyl, β-hydroxypropyl, β-hydroxy-γ-chloropropyl, β-carboxyethyl, β-carbomethyoxyethyl, β-carboethoxyethyl or β-carbobutoxyethyl, β-carbonamidoethyl, β-acetoxyethyl. Dyestuffs of particular interest are those of the formula

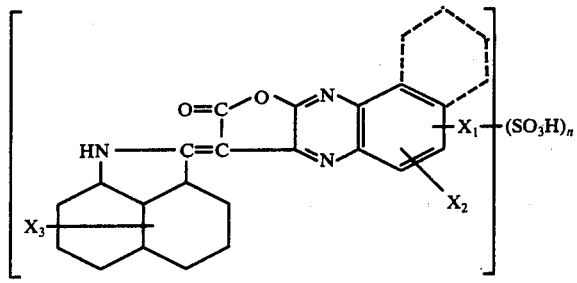

wherein $X_1$ represents fluorine, bromine, chlorine or hydrogen, $C_1$–$C_4$-alkyl, $C_1$–$C_4$-alkoxy, phenyl, phenoxy, thiophenoxy or $C_1$–$C_4$-alkyl sulphonyl, $C_1$–$C_4$-alkylthio, each of which is unsubtituted or substituted by $C_1$–$C_4$-alkoxy, hydroxy, cyano, bromine, chlorine, carbo-$C_1$–$C_4$-alkoxy, $C_1C_4$-alkoxy, $C_1$–$C_4$-alkoxy-$C_1$–$C_4$-alkoxy, $C_1$–$C_4$-alkylcarbonyloxy, chloro-$C_1$–$C_4$-alkylcarbonyloxy or $C_1$–$C_4$-alkoxy-carbonyloxy, fluorine, bromine, chlorine, COOR, in which R represents $C_1$–$C_4$-alkyl or $C_1$–$C_4$-alkyl substituted by $C_1$–$C_4$-alkoxy, hydroxy, cyano, $C_1$–$C_4$-alkylcarbonyloxy, chlorine or bromine, —$SO_2NH$—$C_1$—$C_4$-alkyl and

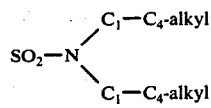

(wherein the $C_1$–$C_4$-alkyl is unsubstituted or substituted by hydroxy, chlorine, bromine, $C_1$—$C_4$-alkoxy or phenyl),
—$SO_2$-alkyl or CN;
$X_2$ represents methoxy, ethoxy, methyl or hydrogen,
$X_3$ represents hydrogen, alkyl containing up to 4 carbon atoms, chlorine, bromine,

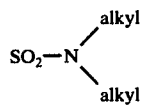

(wherein alkyl is substituted or unsubstituted), nitro, or $SO_2$—R, wherein R represents alkyl or substituted or unsubstituted phenyl, $n$ is 0, 1 or 2, and the dotted ring can represent a fused benzene ring, preferred dyes are those of formulae

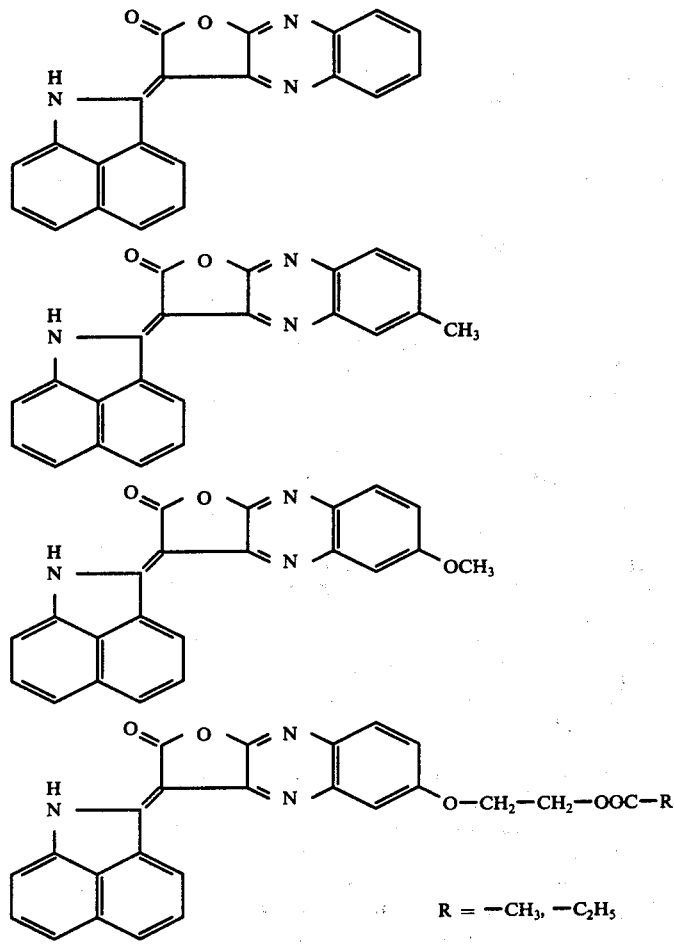

Water-solubilising groups are primarily sulphonic acid groups and groups with positively charged (quaternary) nitrogen atoms. Free carboxyl groups (—COOH) are normally classified among the water-solubilising groups, but as a rule they effect solubility in water only in the form of their salts, for example the alkali salts, so that their exclusion constitutes only a preferred embodiment.

The reaction of the naphtholactam of formula (II) with the acetic ester of formula III which contains active methylene groups takes place in the presence of an acid condensation agent, for example phosphroxy bromide, phosphorus trichloride, phosphorus tribromide, phosphorus pentachloride, thionyl chloride, phosgene (in an autoclave), or mixture of phosphoroxy chloride and phosphorus pentoxide, but in particular in the presence of phosphoroxy chloride.

The reaction takes place advantageously at elevated temperature, for example at temperatures from 50° to 200° C, but preferably in the range from 60° to 130° C. It is advantageously carried out in an inert organic solvent, such as benzene, toluene, xylene, chlorobenzene, dichloriobenzene, nitrobenzene, ethylene chloride, carbon tetrachloride or chloroform. The naphtholactam compound of formula (II) used as starting materials are known. As examples there may be cited: naphtholactam-(1.8), 4-methoxy-naphtholactam-(1.8), 4-bromo-naphtholactam-(1.8), 4-chloro-naphtholactam-(1.8), 2,4-dichloro-naphtholactam-(1.8), 4-nitro-naphtholactam-(1.8), 4-methylsulphonyl-naphtholactam-(1.8), 4-morpholinosulphonyl-naphtholactam-(1.8), 4-methylmercapto-naphtholactam-(1.8), 4-sulpho-naphtholactam-(1.8), 2-methyl-naphtholactam-(1.8).

The starting materials of formula (III) are obtained by condensing phenylenediamines of formula (V)

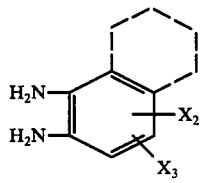

wherein $X_2$ and $X_3$ and the dotted ring have the meanings previously assigned to them, with oxalacetic ester of formula (VI)

RO—OC—CO—CH$_2$—CO—COOR  (VI)

wherein R preferably represents a lower alkyl group. The condensation product can be illustrated by the formula

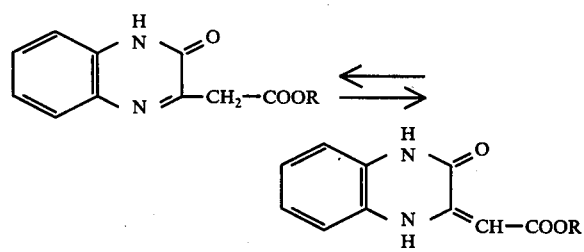

Suitable diamines are:

o-phenylenediamine
1,2-diamino-4-methylbenzene
1,2-diamino-3-methylbenzene
1,2-diamino-4,6-dimethylbenzene
1,2-diamino-4-cyanobenzene
1,2-diamino-4-methoxybenzene
1,2-diamino-3-methoxybenzene
1,2-diamino-4-acetylaminobenzene
1,2-diamino-(3- or 4-)-ethoxybenzene
1,2-diamino-(3- or 4)-propoxybenzene
1,2-diamino-3- or 4-(1,2-epoxypropoxy)-benzene
1,2-diamino-4-nitrobenzene
1,2-diamino-4-chloro-5-ethoxybenzene
1,2-diamino-naphthalene
1,2-diamino-4-chlorobenzene
1,2-diamino-4-bromobenzene
1,2-diamino-4-N-(ethyl-, β-hydroxyethyl)- or β-acyloxyethyl)benzene or
1,2-diamino-4-N,N-diethylaminobenzene.

Suitable oxalylacetic esters are above all the lower alkyl esters. The subsequent sulphonation of compounds of the formula (I) which do not contain sulphonic acid groups is advantageously carried out with customary sulphonation agents, preferably with oleum containing 5–60% of $SO_3$, so as to introduce one to two sulpho groups. The process is desirably carried out at temperatures between 5° and 50° C by known methods.

The dyes of formula (I) yield brilliant, luminous orange to red dyeings, which fluoresce as a rule in ultraviolet light and possess outstanding fatness properties. The dyes which do not contain water-solubilising groups are particularly useful.

The new dyestuffs are suitable for dyeing regenerated man-made and synthetic man-made fibres, for example acrylic or acrylonitrile fibres, polyacrylonitrile fibres and copolymers of acrylonitrile and other vinyl compounds, such as acrylic esters, acrylic amides, vinyl pyridine, vinyl chloride, or vinylidene chloride, copolymers of dicyanoethylene and vinyl acetate, and of acrylonitrile block copolymers, fibres of polyurethane, polyolefins, such as basically modified polypropylene, polypropylene modified with nickel or unmodified polypropylene, cellulose triacetate and cellulose 2½-acetate, and especially fibres of polyamides, such as nylon 6, nylon 6 6 or nylon 12, and of aromatic polyesters, such as those of terephthalic acid and ethylene glycol or 1,4-dimethylolcyclohexane and copolymers of terephthalic acid and isoterephthalic acid with ethylene glycol.

The dyeing of the above mentioned fibre materials with the dyes according to the invention which are sparingly soluble in water, is carried out preferably from aqueous dispersion. It is appropriate, therefore, to finely divide the compounds suitable for use as disperse dyes by grinding them with textile assistants, for example dispersants, and possibly with other grinding assistants. By subsequent drying, dyestuff preparations are obtained consisting of textile assistant and the dye.

Examples of dispersants of the non-ionic group that can be used with advantage are: addition products of 8 moles of ethylene oxide with 1 mole of p-tert.-octylphenol, of 15 or 6 moles of ethylene oxide with castor oil, of 20 moles of ethylene oxide with the alcohol $C_{16}H_{33}OH$, ethylene oxide addition products with di-[β-phenylethyl]-phenols, polyethylene oxide-tert.-dodecyl-thioether, polyamine-polyglycol ether or addition products of 15 or 30 moles of ethylene oxide with 1 mole of the amine $C_{12}H_{25}NH_2$ or $C_{18}H_{37}NH_2$.

As anionic dispersants there may be mentioned: sulphuric acid esters of alcohols of the fatty series containing 8 to 20 carbon atoms, of the ethylenoxy adducts of the corresponding fatty acid amides, or of alkylated phenols containing 8 to 12 carbon atoms in the alkyl moiety: sulphonic acid esters with alkyl radicals containing 8 to 20 carbon atoms; sulphation products of unsaturated fats and oils; phosphoric acid esters containing 8 to 20 carbon atoms; fatty acid soaps, also alkylaryl sulphonates, condensation products of formaldehyde with naphthalenesulphonic acid and lignin sulphonates.

Suitable cationic dispersants are quaternary ammonium compounds that contain alkyl or aralkyl radicals of 8 to 20 carbon atoms.

In addition to containing the dispersants, the dyestuff preparations can contain organic solvents, especially solvents that boil above 100° C, which are preferably miscible with water, such as mono- and dialkylglycol ether, dioxan, dimethyl formamide or dimethyl acetamide, tetramethylenesulphone or dimethyl sulphoxide. Dye, dispersant and solvent can with advantage be ground together.

Such a dyestuff preparation is obtained, for example, by working 2 to 30, preferably 5 to 20, percent by weight of the dispersant with 10 to 55 percent by weight, preferably about two to four times the amount, of dye, and about 10 to 20 parts of a glycol or of another water retardant, into a paste. The pH is then adjusted to about 9 with a dilute acid, preferably with sulphuric or acetic acid, and the paste is then bulked with water to 100%. The mixture is subsequently ground to the required degree of fineness, for example in a glass bead mill or another dispersing machine, at a temperature between 20° and 90° C.

The polyester fibres are dyed from aqueous dispersion with the dyes according to the invention, which are sparingly soluble in water, according to the conventional processes for polyester material. Polyesters of aromatic polycarboxylic acids with polyfunctional alcohols are dyed preferably at temperatures of over 100° C under pressure. However, the dyeing can also be carried out at the boiling point of the dye bath in the presence of dyestuff carriers, for example phenylphenols, polychlorobenzene compounds or similar assistants, or by the thermosol process, that is to say padding with subsequent after-treatment with the application of heat, for example thermofixing, at 180°-210° C. Cellulose 2½-acetate fibres are dyed preferably at temperatures of 80°-85° C, whereas cellulose triacetate fibres are dyed advantageously at the boiling point of the dye bath. The use of dyestuff carriers is superfluous in dyeing cellulose 2½-acetate or polyamide fibres. The dyes according to the invention can also be used for printing the materials mentioned according to conventional methods.

The dyeings obtained according to the process of the present invention can be subjected to an aftertreatment, for example by heating with an aqueous solution of an ion-free detergent.

According to the process of the present invention, the cited compounds can also be applied by printing instead of by impregnating. This is accomplished by using, for example, a printing ink which contains the finely dispersed dye in addition to the customary assistants used in the printing industry, such as wetting agents and thickeners.

Furthermore, it is possible to dye, for example, synthetic fibres, such as polyesters and polyamides, in organic solvent liquors, for example a mixture of perchloroethylene and dimethyl formamide or in pure perchloroethylene.

According to the process of the present invention, strong, brilliant dyeings and prints with excellent fastness properties are obtained, especially fastness to light, thermofixation, sublimation, pleating, exhaust gas, cross-dyeing, dry-cleaning, ironing, rubbing, chlorine, and good wet fastness properties, for example fastness to water, washing and perspiration.

It is also possible to use the new water-insoluble dyes for the spin dyeing of polyamides, polyesters and polyolefins. The polymers to be dyed are advantageously in the form of powder, grains of chips, as ready prepared spinning solution or mixed in the fused state with the dye, which is introduced in the dry state or in the form of a dispersion or solution in an optionally volatile solvent. After the dye has been uniformly distributed in the solution or the melt of the polymer, the mixture is processed in known manner by pouring, moulding or extruding to fibres, yarns, monofilaments, films and the like. p The dyes of the present invention are preeminently suitable for colouring oils of macromolecular materials such as varnishes, films, sheets and mouldings, for example those of cellulose esters, such as cellulose 2½-acetate and cellulose triacetate, polyvinyl compounds, such as polyvinyl chloride, polyvinyl acetate; polyurethanes, polystyrene, polyesters, polyamides and polycarbonates in the melt/spinning solution. The non-saltlike compounds of formula (I) are particularly suitable for this utility, as well as those compounds which contain sulpho groups which are in the form of salts of suitable organic cations, for example those of fat-solubilising alkylamines or basic dyes.

The dyes of the present invention also possess excellent lightfastness properties in bright dyeing, and in combination with other disperse dyes they have great brilliance (fluorescence), excellent fastness to sublimation, low carrier sensitivity in respect of the lightfastness and very high colour strength combined with good reserve for other fibres, for example wool fibres. They also have only a low pH sensitivity and are very suitable in particular for the high temperature and thermosol processes, as well as for the permanent press finish ("Korotron" process). They are furthermore suitable for printing by all conventional methods, including the printing of blends.

They have excellent lightfastness, good heat resistance and good solubility in dope dyeing (especially of polyester spinning solutions/melts). While possessing excellent fastness to migration, they do not migrate to the surface when the fibres undergo heat treatments (e.g. during texturising), and they have good fastness to rubbing.

The invention is illustrated by the following Examples, in which the parts and percentages are by weight unless otherwise indicated.

EXAMPLE 1

At a temperature of 100° C, 8.75 g of phosphoroxy chloride are added dropwise in the course of 30 minutes to a mixture containing 8.50 g of naphthostyril and 11.60 g of the compound of formula

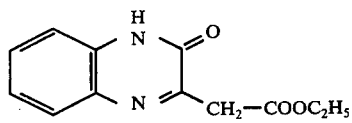

in 75 ml of chlorobenzene, and the reaction mixture is subsequently stirred for 15 minutes at the same temperature. The reaction mixture is then allowed to cool and the precipitate which has formed is filtered off at 30° C and mixed with chlorobenzene. The precipitate is then suspended in 100 ml of chlorobenzene and 4 ml of pyridine are added, so that the mixture shows neutral reaction. After the mixture has been stirred for 30 minutes at room temperature the dye is filtered off and washed firstly with chlorobenzene and then with methanol, to yield the dye of the probable formula

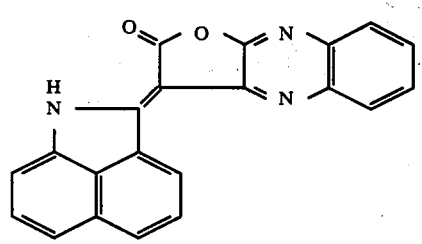

in the form of a brick-red powder which dissolves in dimethyl formamide in a bluish red colour. When this dye is ground with dispersants in the manner normally employed for disperse dyes, a dyeing preparation is obtained with which it is possible to effect red dyeings of great brilliance, excellent lightfastness and a good fastness to sublimation on polymethylene glycol terephthalate.

By repeating the above procedure, but using instead of the above heterocyclic compound an equivalent amount of the mixture of the compounds

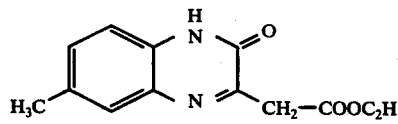

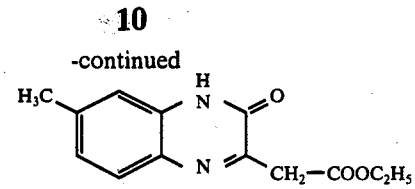

(obtained by reacting 4-methyl-1,2-phenylenediamine with oxalacetic ester), a mixture of the dyes of the probable formulae

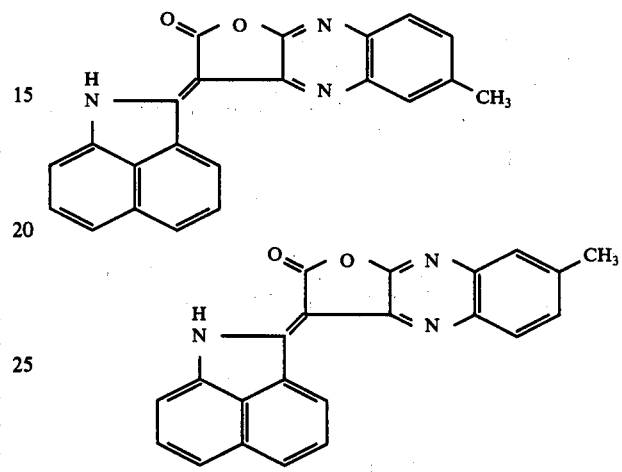

is obtained. When applied as disperse dyes to polymethylene glycol terephthalate, they produce brilliant red dyeings with good fastness to light and sublimation. By repeating the same procedure, but using the heterocyclic compounds listed in column I of the table (obtained from the corresponding 1,2-phenylenediamines and oxalacetic ester, but shown in only one of the possible isomeric forms), the dyes listed in column II are obtained. When applied as disperse dyes, these also produce brilliant red dyeings with good fastness to light and sublimation on polyethylene glycol terephthalate.

Table I

| Ex No | I | II | Shade on PET* |
|---|---|---|---|
| 2 | H₃CO—[quinoxalinone]—CH₂—COOC₂H₅ | [naphthyl-NH-CH=]—[oxazine fused]—OCH₃ | red |
| 3 | H₅C₂O—[quinoxalinone]—CH₂—COOC₂H₅ | [naphthyl-NH-CH=]—[oxazine fused]—O—C₂H₅ | red |
| 4 | (H₃C)₂CH—O—[quinoxalinone]—CH₂—COOC₂H₅ | [naphthyl-NH-CH=]—[oxazine fused]—O—CH(CH₃)₂ | red |

Table I-continued

| Ex No | I | II | Shade on PET* |
|---|---|---|---|
| 5 | [structure: 6-(sec-butoxy)-quinoxalin-2(1H)-one with CH₂-COOC₂H₅] | [structure with sec-butoxy substituent and naphthylamine] | red |
| 6 | [structure: 6-(isobutoxy)-quinoxalin-2(1H)-one with CH₂-COOC₂H₅] | [structure with isobutoxy substituent and naphthylamine] | red |
| 7 | [structure: 6-ethyl-quinoxalin-2(1H)-one with CH₂-COOC₂H₅] | [structure with ethyl substituent and naphthylamine] | red |
| 8 | [structure: 6-isopropyl-quinoxalin-2(1H)-one with CH₂-COOC₂H₅] | [structure with isopropyl substituent and naphthylamine] | red |
| 9 | [structure: 6-chloro-7-methoxy-quinoxalin-2(1H)-one with CH₂-COOC₂H₅] | [structure with Cl, OCH₃ and naphthylamine] | bluish red |
| 10 | [structure: 6,7-dimethoxy-quinoxalin-2(1H)-one with CH₂-COOC₂H₅] | [structure with two OCH₃ and naphthylamine] | reddish violet |
| 11 | [structure: 6-chloro-quinoxalin-2(1H)-one with CH₂-COOC₂H₅] | [structure with Cl and naphthylamine] | red |
| 12 | [structure: 6-bromo-quinoxalin-2(1H)-one with CH₂-COOC₂H₅] | [structure with Br and naphthylamine] | red |
| 13 | [structure: 5,7-dimethyl-quinoxalin-2(1H)-one with CH₂-COOC₂H₅] | [structure with two CH₃ and naphthylamine] | red |

Table I-continued

| Ex No | I | II | Shade on PET* |
|---|---|---|---|
| 14 | 8-methyl-quinoxalin-2(1H)-one-3-yl-CH₂—COOC₂H₅ | corresponding condensation product with 1,8-naphthalene structure | red |
| 15 | 6,7-dimethyl-quinoxalin-2(1H)-one-3-yl-CH₂—COOC₂H₅ | " | red |
| 16 | 6-(ClC₂H₄O)-quinoxalin-2(1H)-one-3-yl-CH₂—COOC₂H₅ | " | red |
| 17 | 6-(CH₃COO—C₂H₄—O)-quinoxalin-2(1H)-one-3-yl-CH₂—COOC₂H₅ | " | red |
| 18 | 6-(C₂H₅COO—C₂H₄—O)-quinoxalin-2(1H)-one-3-yl-CH₂—COOC₂H₅ | " | red |
| 19 | 6-(ClC₂H₄—COO—C₂H₄—O)-quinoxalin-2(1H)-one-3-yl-CH₂—COOC₂H₅ | " | red |
| 20 | 6-(C₂H₅OOC—O—C₂H₄—O)-quinoxalin-2(1H)-one-3-yl-CH₂—COOC₂H₅ | " | red |
| 21 | 6-((CH₃)₂CH—OOC—O—C₂H₄—O)-quinoxalin-2(1H)-one-3-yl-CH₂—COOC₂H₅ | " | red |
| 22 | 6-(ClCH₂—COO—C₂H₄—O)-quinoxalin-2(1H)-one-3-yl-CH₂—COOC₂H₅ | " | red |
| 23 | 6-(CH₃COO—C₂H₄—S)-quinoxalin-2(1H)-one-3-yl-CH₂—COOC₂H₅ | " | red |

Table I-continued

| Ex No | I | II | Shade on PET* |
|---|---|---|---|
| 24 | (quinoxalinone with S-C₂H₄-OOC-C₂H₅ and CH₂-COOC₂H₅) | (naphthyl-amino coupled structure with S-C₂H₄-OOC-C₂H₅) | red |
| 25 | (quinoxalinone with S-C₂H₄-OOC-C₂H₄-Cl and CH₂-COOC₂H₅) | (coupled structure with S-C₂H₄-OOC-C₂H₄-Cl) | red |
| 26 | (quinoxalinone with S-C₂H₄-OOC-CH₂Cl and CH₂-COOC₂H₅) | (coupled structure with S-C₂H₄-OOC-CH₂Cl) | red |
| 27 | (quinoxalinone with S-C₂H₄-O-COOC₂H₅ and CH₂-COOC₂H₅) | (coupled structure with S-C₂H₄-O-COOC₂H₅) | red |
| 28 | (quinoxalinone with S-C₂H₄-O-COO-CH(CH₃)₂ and CH₂-COOC₂H₅) | (coupled structure with S-C₂H₄-O-COO-CH(CH₃)₂) | red |
| 29 | (quinoxalinone with H₃OOC- and CH₂-COOC₂H₅) | (coupled structure with -COOCH₃) | red |
| 30 | (quinoxalinone with H₅C₂OOC- and CH₂-COOC₂H₅) | (coupled structure with -COOC₂H₅) | red |
| 31 | (quinoxalinone with (CH₃)₂CH-COO- and CH₂-COOC₂H₅) | (coupled structure with -COO-CH(CH₃)₂) | red |
| 32 | (quinoxalinone with OC-O-CH(CH₃)-C₂H₅ and CH₂-COOC₂H₅) | (coupled structure with -COO-CH(CH₃)-C₂H₅) | red |
| 33 | (quinoxalinone with OC-O-CH₂-CH(CH₃)₂ and CH₂-COOC₂H₅) | (coupled structure with -COO-CH₂-CH(CH₃)₂) | red |

Table I-continued

| Ex No | I | II | Shade on PET* |
|---|---|---|---|
| 34 | (structure) | (structure) | red |
| 35 | (structure) | (structure) | red |
| 36 | (structure) | (structure) | red |
| 37 | (structure) | (structure) | red |
| 38 | (structure) | (structure) | red |
| 39 | (structure) | (structure) | red |
| 40 | (structure) | (structure) | red |
| 41 | (structure) | (structure) | red |
| 42 | (structure) | (structure) | red |
| 43 | (structure) | (structure) | red |

Table I-continued

| Ex No | I | II | Shade on PET |
|---|---|---|---|
| 44 | (structure) | (structure) | red |
| 45 | (structure) | (structure) | red |
| 46 | (structure) | (structure) | red |
| 47 | (structure) | (structure) | red |
| 48 | (structure) | (structure) | red |
| 49 | (structure) | (structure) | red |
| 50 | (structure) | (structure) | red |
| 51 | (structure) | (structure) | red |
| 52 | (structure) | (structure) | red |

Table I-continued

| Ex No | I | II | Shade on PET* |
|---|---|---|---|
| 53 | [structure: naphthoquinoxalinone with CH₂COOC₂H₅ substituent] | [structure: fused heterocyclic dye with naphthylamine moiety] | red |

*polyethylene glycol terephthalate

EXAMPLE 54

A mixture of 4 g of the naphthostyril of formula

[structure: 6-methoxy-naphthostyril, HN, O, OCH₃]

5 g of the compound of formula

[structure: H₃C-benzene fused with H-N, N ring, CH₂—COOC₂H₅]

3.50 g of phosphoroxy chloride and 30 ml of chlorobenzene is stirred for 30 minutes at a temperature of 100° C, whereupon the dye that has formed is isolated as described in Example 1. The resultant dye of formula

[structure: dye with OCH₃, naphthyl-NH, fused rings, CH₃]

colours polymethylene glycol terephthalate from a dispersion in a brilliant red shade with good fastness to light and sublimation.

A dye possessing similar properties is obtained by repeating the same procedure, but using equivalent amounts of the corresponding ethoxynaphthostyril instead of methoxynaphthostyril.

Dyes with similar properties are also obtained by using in both cases equivalent amounts of the compound of formula

[structure: H₃CO-benzene-HN-N ring with CH₂—COOC₂H₅]

instead of the above-mentioned heterocyclic compound.

EXAMPLE 55

A mixture consisting of 5 g of the compound of formula

[structure: HN, O, Br-substituted naphthostyril]

8.3 g of the compound of formula

[structure: benzene fused ring with SO₂—NH(CH₂)₃—O—CH(CH₃)₂ group and CH₂—COOC₂H₅]

3.50 l g of phosphoroxy chloride and 40 ml of chlorobenzene is stirred for 30 minutes at a temperature of 100° C, whereupon the dye that has formed is isolated as described in Example 1.

The resultant dye of formula

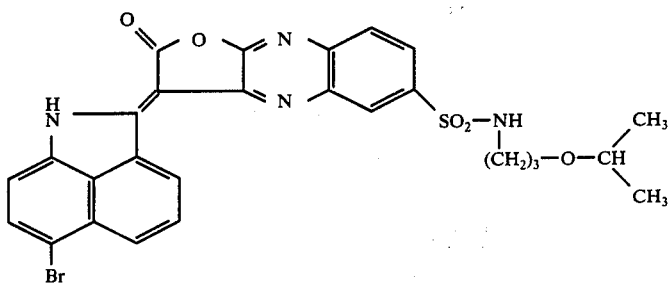

colours plastics and polyethylene glycol terephthalate red in the melt. The colourations are fast to light and sublimation.

A dye possessing similar properties is obtained by carrying out the above procedure, but using an equivalent amount of the chloronaphthostyril of formula

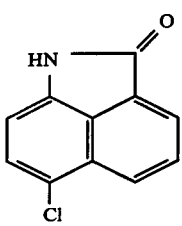

instead of bromonaphthostyril.

Dyes with similar properties are also obtained by using instead of bromonaphthostyril equivalent amounts of the naphthostyrils of formula

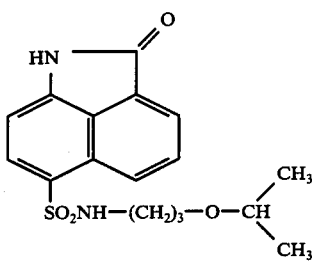

or

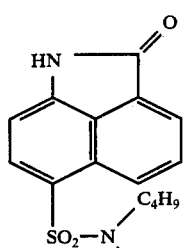

or

-continued

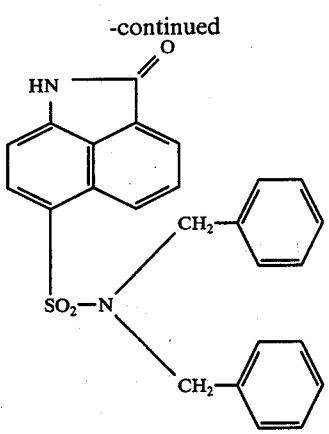

or

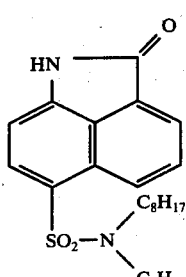

EXAMPLE 56

A mixture consisting of 3.50 g of naphthostyril, 8.30 g of the compound of formula

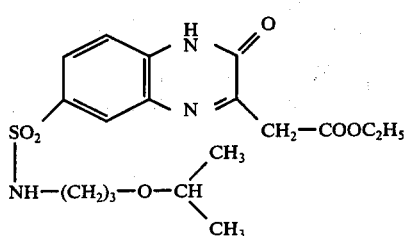

3.50 g of phosphoroxy chloride and 40 ml of chlorobenzene is stirred for 30 minutes at a temperature of 100° C, whereupon the dye of formula

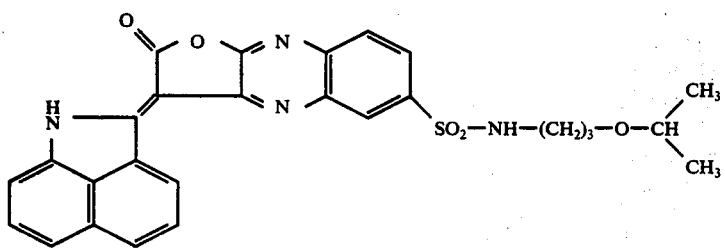

is isolated as described in Example 1. The dye colours acetate rayon in the spinning solution/melt red with excellent colour strength and good lightfastness.

Dyes which colour plastics or polyethylene glycol terephthalate red in the spinning solution/melt are obtained by using instead of the above compound equivalent amounts of the compounds of formula

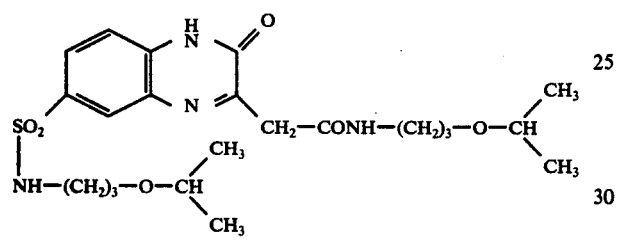

[obtained from the compound mentioned at the start of this example by aminolysis with the amine $CH_2N—(CH_2)_3—O-CH(CH_3)_2$], or

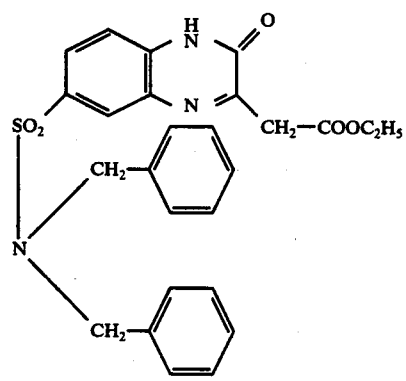

or

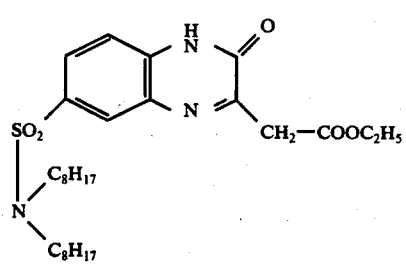

EXAMPLE 57

A mixture consisting of 7 g of the compound of formula

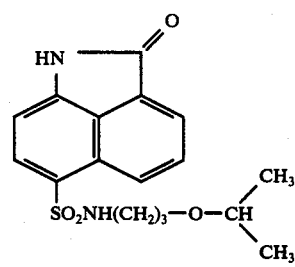

4.7 g of the compound of formula

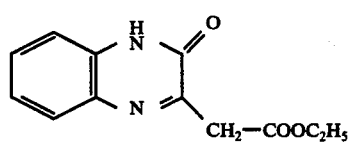

3.50 g of phosphoroxy chloride and 30 ml of chlorobenzene is stirred for 30 minutes at 100° C, whereupon the dye of formula

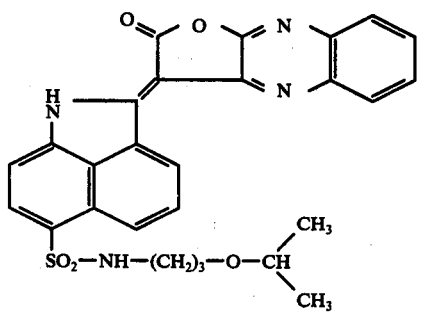

is isolated in the manner described in Example 1. This dye colours acetate rayon red in the melt/spinning solution. The colourations are strong and have good lightfastness.

EXAMPLE 58

2 g of the dye obtained in Example 1 of formula

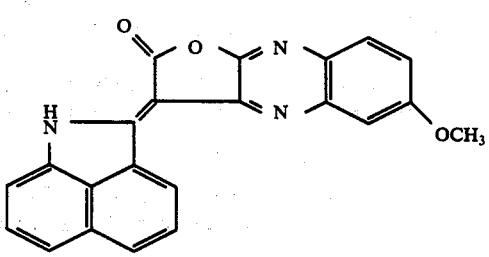

(mixture of two isomers, only one of which is shown) are dispersed in 4000 g of water. To this dispersion are added as swelling agent 12 g of the sodium salt of o-phenylphenol and 12 g of diammonium phosphate and 100 g of polyethylene glycol terephthalate yarn is dyed therein for 1 ½ hours at 95°–98° C. The dyed yarn is rinsed and given an aftertreatment with aqeuous sodium hydroxide and a dispersant. A red dyeing which is fast to washing, light and sublimation is obtained. A red dyeing which has very good fastness to washing and sublimation is obtained by substituting 100 g of cellulose triacetate fabric for the 100 g of polyethylene glycol terephthalate, dyeing under the same conditions, and subsequently rinsing the dyed fabric with water.

EXAMPLE 59

In a pressure dyeing apparatus, 2 g of a dyestuff mixture consisting of equal amounts of each of the dyes of formulae

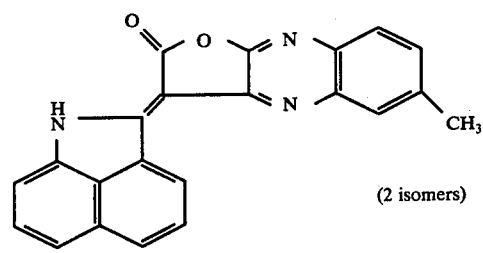

(2 isomers)

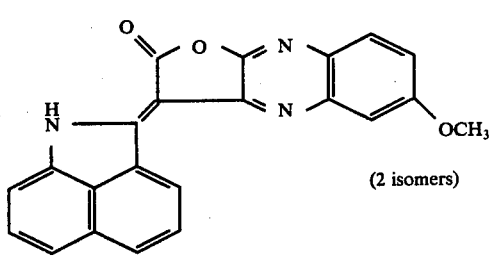

(2 isomers)

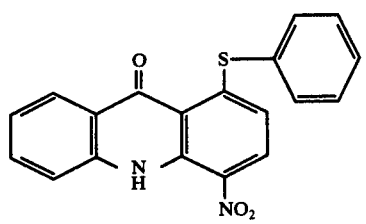

are finely suspended in 4000 g of water which contains 4 g of oleyl polyglcyol ether. The pH of the dyebath is adjusted to 4–5 with acetic acid.

Then 100 g of polyethylene glycol terephthalate fabric are put into this bath, which is heated to 140° C in the course of 30 minutes and dyeing is performed for 50 minutes at this temperature. The dyed fabric is subsequently rinsed, soaped and dried. A scarlet red dyeing which is fast to washing, perspiration, light and sublimation is obtained under these conditions.

The dyes described in the other Examples effect dyeings of equal quality by carrying out this procedure.

EXAMPLE 60

Polyethylene glycol terephthalate fabric is impregnated on a padder at 40° C with a liquor of the following composition:

20 g of the dye obtained in Example 1 of formula

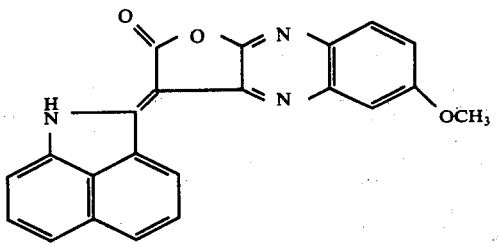

finely dispersed in 7.5 g of sodium alginate,
20 g of triethanolamine,
20 g of octylphenol polyglycol ether and
900 g of water.

The fabric, which is squeezed out to a pick-up of app. 100%, is dried at 100° C and subsequently fixed for 30 seconds at a temperature of 210° C. The dyed goods are rinsed with water, soaped and dried. A red dyeing which is fast to washing, rubbing, light and sublimation is obtained under these conditions.

The dyes described in the other Examples effect dyeing of equal quality by carrying out this procedure.

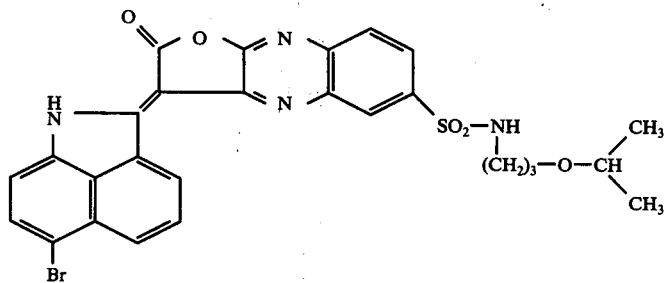

We claim:

1. A dyestuff of the formula

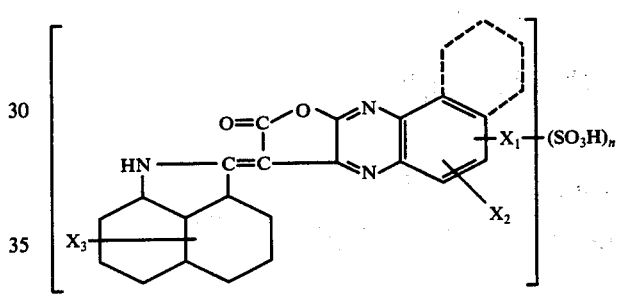

wherein $X_1$ represents fluorine, bromine, chlorine or hydrogen, $C_1$–$C_4$-alkyl, $C_1$–$C_4$-alkoxy, phenyl, phenoxy, thiophenoxy or $C_1$–$C_4$-alkyl sulphonyl, $C_1$–$C_4$-alkylthio, each of which is unsubstituted or substituted by $C_1$–$C_4$-alkoxy, hydroxy, cyano, bromine, chloride, carbo-$C_1$–$C_4$-alkoxy, $C_1$–$C_4$-alkoxy-$C_1$–$C_4$-alkoxy, $C_1$–$C_4$-alkylcarbonyloxy, chloro-$C_1$–$C_4$-alkylcarbonyloxy or $C_1$–$C_4$-alkoxy-carbonyloxy, fluorine, bromine, chlorine, COOR, in which R represents $C_1$–$C_4$-alkyl or $C_1C_4$-alkyl substituted by $C_1$–$C_4$-alkoxy, hydroxy, cyano, $C_1C_4$-alkylcarbonyloxy, chlorine or bromine, —$SO_2NH$-$C_1$–$C_4$-alkyl and

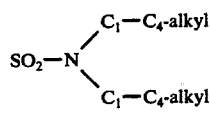

(wherein the $C_1$–$C_4$-alkyl is unsubstituted or substituted by hydroxy, chlorine, bromine, $C_1$–$C_4$-alkoxy or phenyl). —$SO_2C_1$–$C_4$-alkyl or CN;

$X_2$ represents methoxy, ethoxy, methyl or hydrogen.

$X_3$ represents hydrogen, alkyl containing up to 4 carbon atoms, chlorine, bromine,

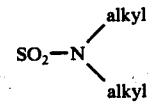

wherein alkyl is substituted or unsubstituted), nitro, or $SO_2$—R, wherein R represents alkyl or substituted or unsubstituted phenyl, $n$ is 0, 1 or 2, and the dotted ring can represent a fused benzene ring.

2. A dyestuff according to claim 1, wherein $n$ is zero.

3. A dyestuff according to claim 2, wherein $X_2$ is hydrogen and $X_1$ and $X_2$ represent hydrogen, $C_1$–$C_1$4-alkyl, or $C_1$–$C_4$-alkyl substituted by $C_1$–$C_4$-alkoxy, hydroxy, cyano, bromine, chlorine, carbo-$C_1$–$C_4$-alkoxy, $C_1$–$C_4$-alkoxy-$C_1$–$C_4$-alkoxy, $C_1$–$C_4$-alkylcarbonyloxy, chloro-$C_1$–$C_4$-alkylcarbonyloxy or $C_1$–$C_4$-alkoxy-carbonyloxy or $C_1$–$C_4$-alkoxy and $X_3$ is hydrogen.

4. A dyestuff according to claim 3, wherein $X_2$ is hydrogen.

5. Dyes according to claim 3, wherein $X_1$ is methyl, a $C_1$–$C_4$-alkoxy or a radical of formula —O—$CH_2CH_2$—O—CO—($C_1$-$C_4$-alkyl).

6. A dyestuff according to claim 1 of the formula

7. A dyestuff according to claim 2 of the formula

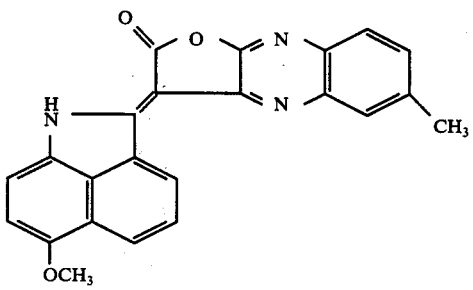

8. A dyestuff according to claim 2 of the formula